United States Patent [19]

Yue et al.

[11] Patent Number: 5,042,455

[45] Date of Patent: Aug. 27, 1991

[54] FLUID WARMER

[75] Inventors: Samuel Yue, Bloomington; Wendell J. Manske, White Bear Lake; John D. Dockter, Eagan, all of Minn.

[73] Assignee: PMT Corporation, Chanhassen, Minn.

[21] Appl. No.: 395,906

[22] Filed: Aug. 18, 1989

[51] Int. Cl.$^5$ ............................................. F24J 1/00
[52] U.S. Cl. .................................. 126/263; 126/204; 62/4; 128/399; 604/113
[58] Field of Search ............... 126/263, 204, 205, 207; 62/4; 128/68.1, 362, 399, 401, 403, DIG. 6; 604/113, 408

[56] References Cited

U.S. PATENT DOCUMENTS

| | | | |
|---|---|---|---|
| 3,542,032 | 11/1970 | Spencer, Jr. ................ | 126/204 X |
| 4,249,923 | 2/1981 | Walda ......................... | 604/113 X |
| 4,366,804 | 1/1983 | Abe ............................. | 126/263 |
| 4,516,564 | 5/1985 | Koiso et al. ................. | 126/204 X |
| 4,532,414 | 7/1985 | Shah et al. .................. | 128/399 X |
| 4,573,447 | 3/1986 | Thrash et al. ............... | 126/263 |
| 4,623,333 | 11/1986 | Fried ............................ | 604/113 X |
| 4,756,299 | 7/1988 | Podella ........................ | 128/399 X |

Primary Examiner—Larry Jones
Attorney, Agent, or Firm—Hugh D. Jaeger

[57] ABSTRACT

A warmer used to warm fluids, such as blood or the like, passed into the human body. Air is introduced through an opened windowed membrane to expose chemicals in a container. A chemical reaction with the air causes a heat reaction of the chemicals. A tube engages in a trough in the container adjacent where the chemical reaction takes place, thereby absorbing the heat of the chemical reaction for warming the fluids, such as blood, saline solution, injectable solutions in trauma, pre-surgical, intra-surgical, post-surgical and any other solutions through the tube.

7 Claims, 7 Drawing Sheets

FLUID WARMER

BACKGROUND OF THE INVENTION

1. Field of the Invention

The present invention pertains to a warming structure, and more particularly, pertains to a warmer used to warm fluids such as passed into the human body or to warm a physical article.

2. Description of the Prior Art

The prior art recognizes warmers, such as in U.S. Pat. No. 3,976,049 to Yamashita et al, entitled "Structure of Warmer" Existing fluid warmers used in the medical field include Futuremed Animec® Infusion Warmer-electrical operation, 2076 Deer Park Avenue, Deer Park, N.Y.; and Level 1 Technologies, Inc. (Level 1 ™ Fluid Warmer) 29 Aldren Road, Plymouth, Mass. However, no patent information is available on these two prior art fluid warmers.

The present invention pertains to a warmer for fluids, particularly fluids for medical applications or procedures, in a new and novel configuration apparatus.

SUMMARY OF THE INVENTION

The present invention pertains to a fluid warmer for the medical field, and more particularly, pertains to a fluid warmer which exports heat from a chemical reaction in a container to an adjacent tube containing a fluid for warming the fluid contained in the tube. The time gradient of the chemical reaction, and thus the temperature, is proportionally controlled by the size of a windowed membrane which allows air to enter and react with the reaction chemical. The product is disposable in any environment, self-contained and does not require any external equipment or materials.

According to one embodiment of the present invention, there is provided a flanged air cavity member and a flanged chemical cavity member sealed to each other with a windowed membrane and an air-permeable member, such as Tyvek, therebetween. The flanged air cavity member is optional, and is not essential to the present invention.

Another embodiment of the present invention would include a blow molded bottle with air-permeable membrane windows and the chemicals contained inside of the bottle. The bottle is molded in such a way as to assume the predetermined geometrical shape molded into the cavity of the bottle so that the bottle engages around or about the desired object to be heated. Two bottles or units can be used together to provide an entire enclosure structure.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
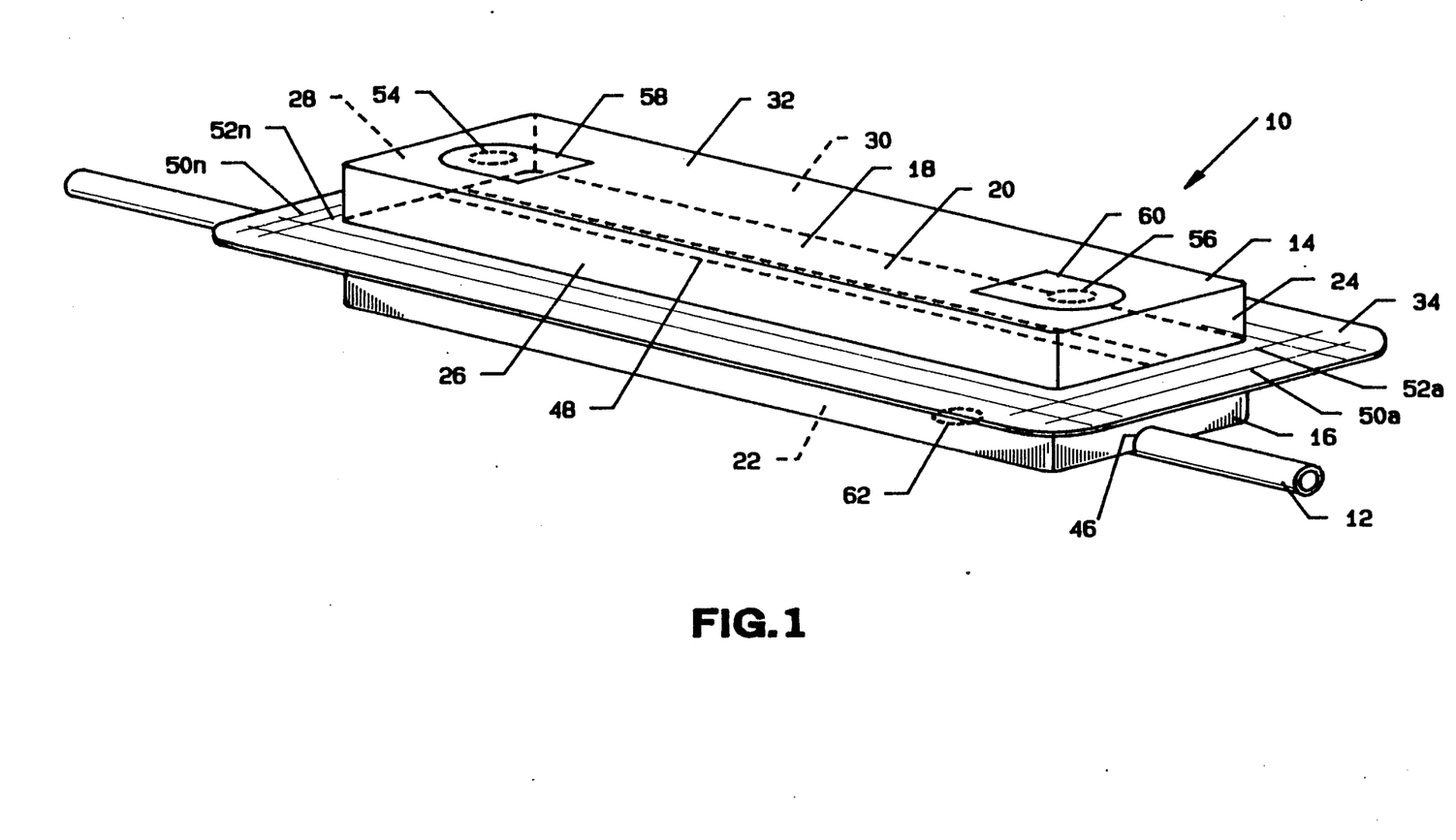
FIG. 1 illustrates a perspective view of a fluid warmer.
Figure 2:
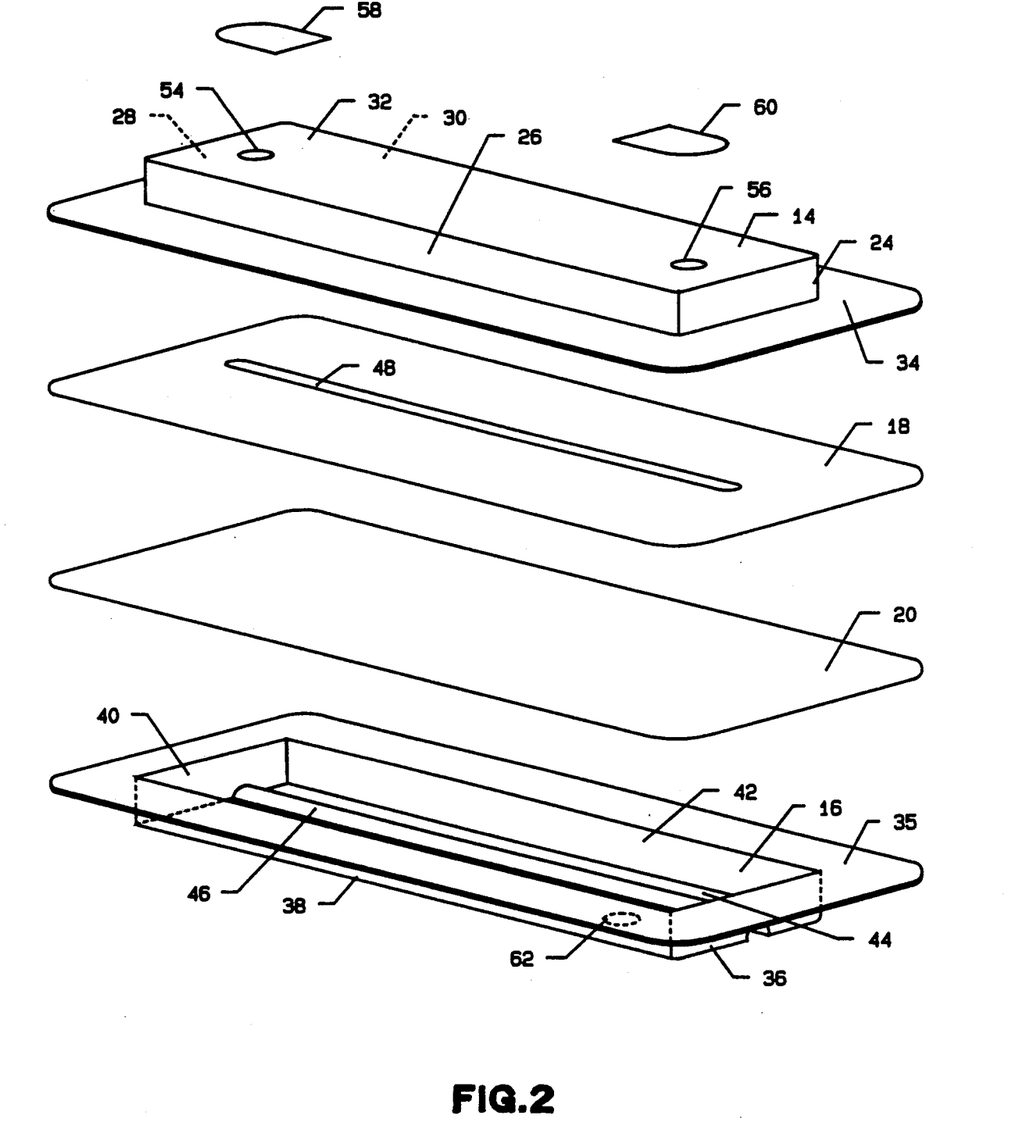
FIG. 2 illustrates an exploded view of FIG. 1.

FIG. 1 illustrates a perspective view of a fluid warmer 10, the present invention. The fluid warmer 10 is illustrated engaging about an IV tube 12, such as for blood or fluids, and includes an air cavity member 14, a chemical cavity member 16, a windowed non-permeable membrane 18, and an air-permeable diaphragm Tyvek, or like, membrane 20 between the air cavity member 14 and the chemical cavity member 16. DuPont Tyvek 1043 is a represented material. A reactive chemical mix 22, as later described, is contained in the chemical cavity member 16 for reaction with ambient air as later explained in detail. The rectangularly shaped air cavity member 14 is of a heat and chemical resistant plastic material, as later described, and includes sides 24–30 and top 32. The cavity member 14 may be shaped in any other geometrical configuration. The cavity is also optional. The air cavity member 14 intersects an upper planar flange member 34. The chemical cavity member 16, as also illustrated in FIG. 2, is also of a heat and chemical resistant plastic, as later described, and includes sides 36–42 and a bottom 44. The chemical cavity 16 intersects a lower planar flange member 35. A trough 46 runs longitudinally, or in any other geometrical configuration desired, with multiple pathways along the length of the bottom 44 to accommodate the IV tube 12 for subsequent heating thereof. The windowed non-permeable membrane 18 includes an elongated aperture or apertures 48 of open cross-sectional area which can be constructed in varying dimensions as to effect surface area and to effect different temperatures and temperature duration within the fluid warmer 10 as later described. The windowed non-permeable membrane 18 and the air-permeable diaphragm membrane 20 are contained and sealed between the air cavity member 14 and the chemical cavity member 16, and also between the upper planar flange member 34 and the lower planar flange member 35. Sealing is accomplished by a plurality of double heat sealed seams 50a–50n and 52a–52n which seal the upper and lower flanges 34 and 35, thereby forming a barrier. Also, the non-permeable membrane 18 may serve as the outside surface, thereby excluding the air cavity member 14. Any other suitable processes such as glueing, ultrasonic bonding, or other processes may be used to effect a tight seal between the air cavity member 14 and the chemical cavity member 16, and the non-permeable membrane 18 and the air-permeable membrane 20. Holes 54 and 56 in the top 32 of the air cavity member 14 allow ambient air to enter the air cavity member 14 when pressure sensitive adhesive tape sealing tabs 58 and 60, which are affixed over holes 54 and 56, are removed by pealing away to allow air into the air cavity member 14, through the aperture 48, in the windowed non-permeable membrane 18, through the air-permeable diaphragm membrane 20, and into the reactive chemical mix 22 in the chemical cavity member 16 to react with the reactive chemical mix 22 to cause heat to be generated. A typical IV tube 12 engaged in the trough 46 and the fluid passing through it are heated by the internally generated heat of the fluid warmer 10. The reactive chemical mix 22 can be a combination of calcium chloride $CaCl_2$ and iron powder or other chemicals which when exposed to air generate heat by way of example and for purposes of illustration only, and not to be construed as limiting of the present invention. The $CaCl_2$ is a deliquescent. Activated charcoal is used as a catalyst. The chemical reaction is described as:

Chemical Reaction $$H_2O + Fe + O_2 \rightarrow Fe_2O_3 + heat$$

One example of a chemical charge is now set forth below in Table 1 as an example and the concentrations and chemicals can vary as so determined, as well as total quantity for varying volumes to be filled.

TABLE 1

|  | Specific Formulation | Ranges By Weight |
|---|---|---|
| Iron Powder | 10 grams | 15%–40% |
| Activated Charcoal | 7 grams | 5%–30% |
| $CaCl_2.H_2O$ Calcium Chloride.Dihydrate | 4 grams | 5%–20% |
| Dried Wood Flour | 19 grams | 20%–40% |
| Water | 7 grams | 10%–30% |
| Nitrogen - packages the above as a dry charge | | |

The heat and chemical resistant polymer material is now set forth below in Table 2.

TABLE 2

| 10 mil Co-Polyester (or PVC, Polystyrene, Polycarbonate, and any other applicable material) |
| 3.5 lbs/ream saran |
| 2 mil polyethylene |

This material provides 0.8cc oxygen at 1000in2 per 24 hours at 73° F. and at 50% R.H., other characteristics may also be acceptable. Other materials can be utilized to obtain the same result. The saran and polyethylene are optional components.

The chemical composition details are now set forth in Table 3.

TABLE 3

1. Activated Carbon, Activated Charcoal
   High absorptivity for many gases, vapors, colloidal solids.
   Obtained by destructive distillation of wood, nut shells, animal bones, etc. Activated by heating to 800–900° C. with steam or $Co_2$ which results in a porous internal structure with area of about 10,000 ft²/gm. Not effective in removing ethylene. Capable of absorbing large amounts of water vapor. A catalyst and a catalyst carrier. Organic vapors tend to displace any water present on the carbon.
2. Calcium Chloride $CaCl_2$, $CaCl_2.H_2O$, $CaCl_2.2H_2O$, $CaCl_2.6H_2O$ Drying and desiccating agent. White deliquescent crystals. Other desiccating agents may also be used.
3. Iron Powder
   Highly reactive chemically, a strong reducing agent, oxidizes readily in moist air. Dusts suspended in air are flammable and an explosion risk. A dietary supplement essentially non-toxic.
4. Tyvek - Spunbonded Olefin.

One example of dimensions for the warmer are $1'' \times 1\frac{1}{2}'' \times 6$.

An additional hole 62 in the chemical cavity member 16 is for injection of the reactive chemical mix 22 into the chemical cavity member during manufacturing. The chemical mixture may be added before the body is assembled and then the hole 62 in the chemical cavity member 16 is not essential for filling.

FIG. 2 illustrates an exploded view of the fluid warmer where all numerals correspond to those elements previously described. The aperture 48 is illustrated in more detail and is later described. This is one configuration of the aperture or apertures, and other geometrical configurations are within the scope of the teaching of this disclosure.

Figure 3:
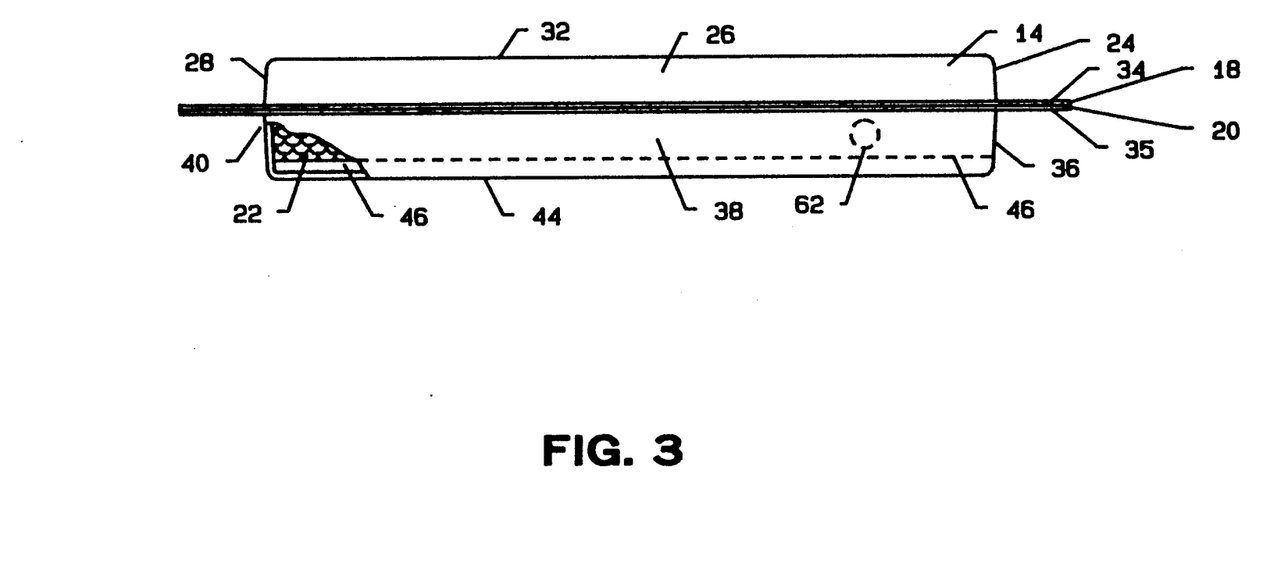
FIG. 3 illustrates a side view of FIG. 1.

FIG. 3 illustrates a side view partially cutaway of the fluid warmer 10 where all numerals correspond to those elements previously described.

Figure 4:
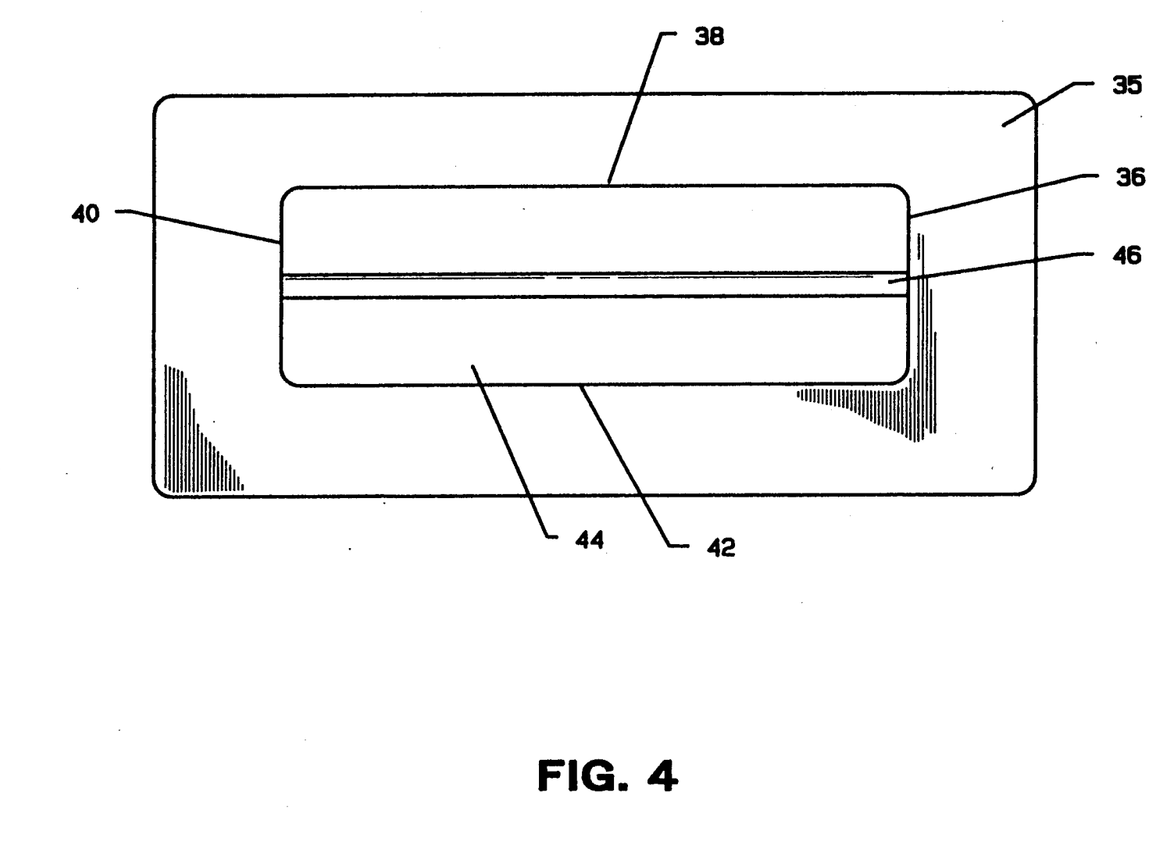
FIG. 4 illustrates a bottom view of FIG. 1.

FIG. 4 illustrates a bottom view of the fluid warmer 10 where all numerals correspond to those elements previously described. An IV tube 12 engages into and about the semicircular trough 46.

MODE OF OPERATION

The warmer 10 is manufactured as now set forth. First, the chemical reaction mix filled into the cavity. Second, the cavities are heat sealed together, forming a barrier about the air-permeable membrane by the air cavity member and the chemical cavity member. Third, the warmer is positioned in a vacuum chamber, a vacuum is pulled, and then broken by flooding the chamber with nitrogen. Fourth, a proper amount of water is introduced through the holes. Fifth, the holes 54 and 56 are tape sealed.

A fluid tube, such as an IV tube or a blood tube, can be laid into the trough 46. The tabs 58 and 60 are pealed away, and heat is generated on exposure of the reactive chemical mix 22 to air.

If the optional air cavity member 14 is not used, the warmer is placed in a non-permeable pouch with the water, then evacuated and flooded with nitrogen. The non-permeable pouch is then sealed shut so that it is air tight. To utilize the warmer, time must be allowed for the water to be absorbed. The pouch is torn open and exposed to air, allowing the warmer to heat up. An IV tube is then placed in the trough.

DESCRIPTION OF A FIRST ALTERNATIVE EMBODIMENTS

Figure 5:
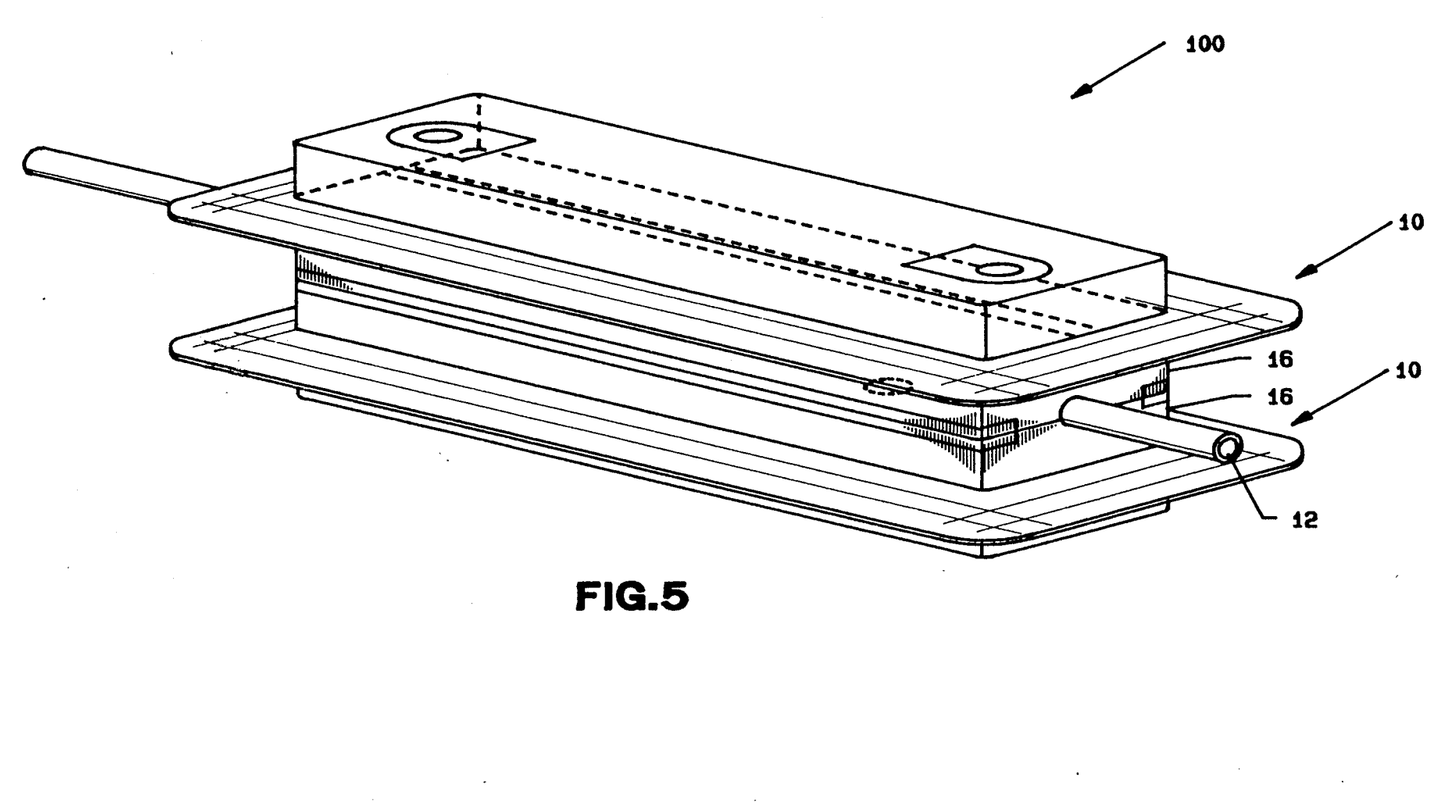
FIG. 5 illustrates a first alternative embodiment of two fluid warmers placed back-to-back with respect to each other.

FIG. 5 illustrates a first alternative embodiment 100 where the chemical cavity member 16 of two fluid warmers 10 are placed back-to-back over and encompassing an IV tube 12 to heat the entire circumference of the IV tube 12 for increased heating capabilities. Different capabilities may be utilized by different cross-sectional areas of the apertures 48 in each of the fluid warmers. The first fluid warmer could contain a large aperture 48 for rapid heating, and the second fluid warmer could contain a small apertures 48 for sustaining heat throughout a period of time. Other possibilities exist such as providing a V-shaped aperture for rapid chemical reaction at one end of a fluid warmer where the V is widest, and a slower chemical reaction at the other end of the fluid warmer where the V is narrower.

Additional exit sites can be placed in the shell of the warmer so a fluid tube can be placed in varying path lengths on the warmer, thereby altering the amount of heating.

Figure 6:
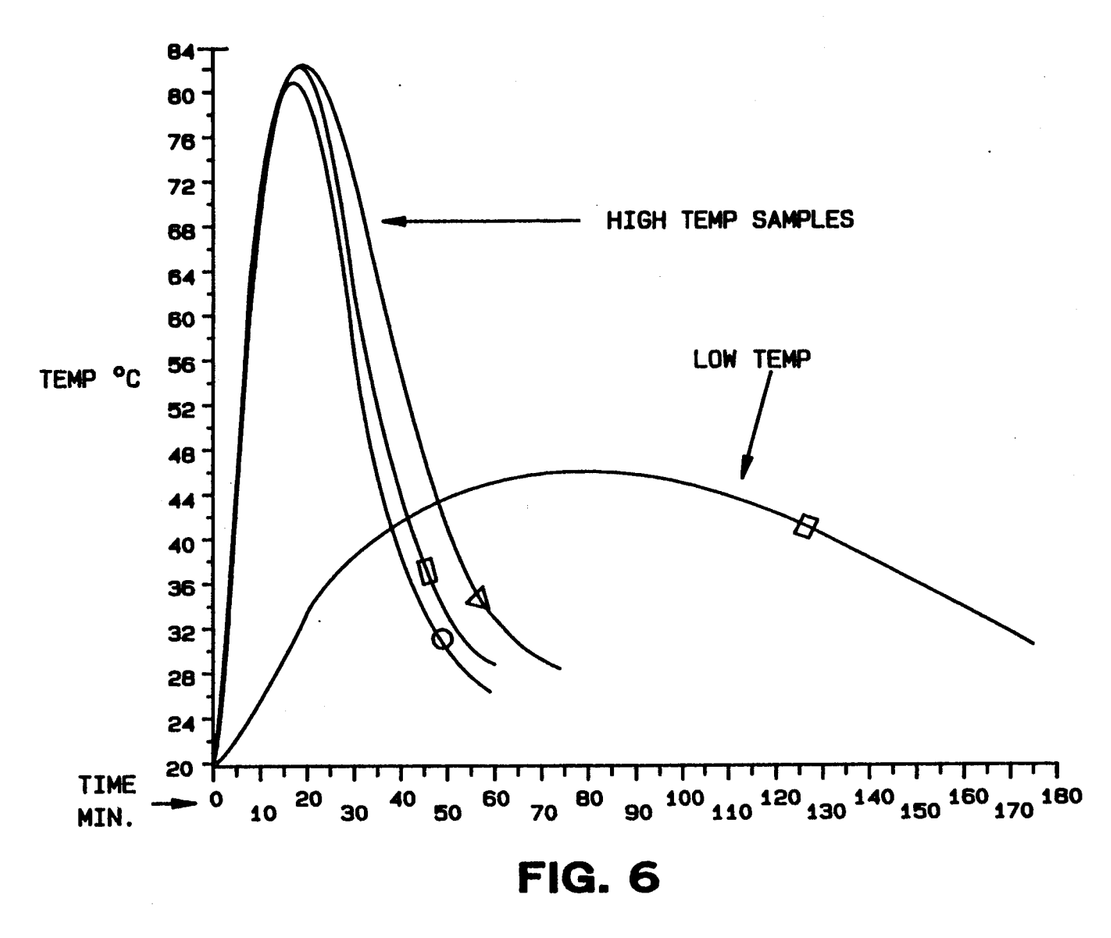
FIG. 6 illustrates a graph and pictorial of temperature versus time for different aperture openings which will change when the chemical concentrations are altered and are warmer surface temperatures; and, FIG. 7 illustrates a second alternative embodiment of a fluid warmer.

FIG. 6 illustrates two curves of temperature versus time for different cross-sectional areas of the aperture 48. Aperture of other cross-sectional areas provides different temperature versus time curves. Heat transfer automatically commences on removal of the tabs, and exposes the chemical mix to air initiating a heat reaction. Varying chemical concentration mixtures and volumes would also change the temperature versus time curves.

DESCRIPTION OF A SECOND ALTERNATIVE EMBODIMENTS

Figure 7:
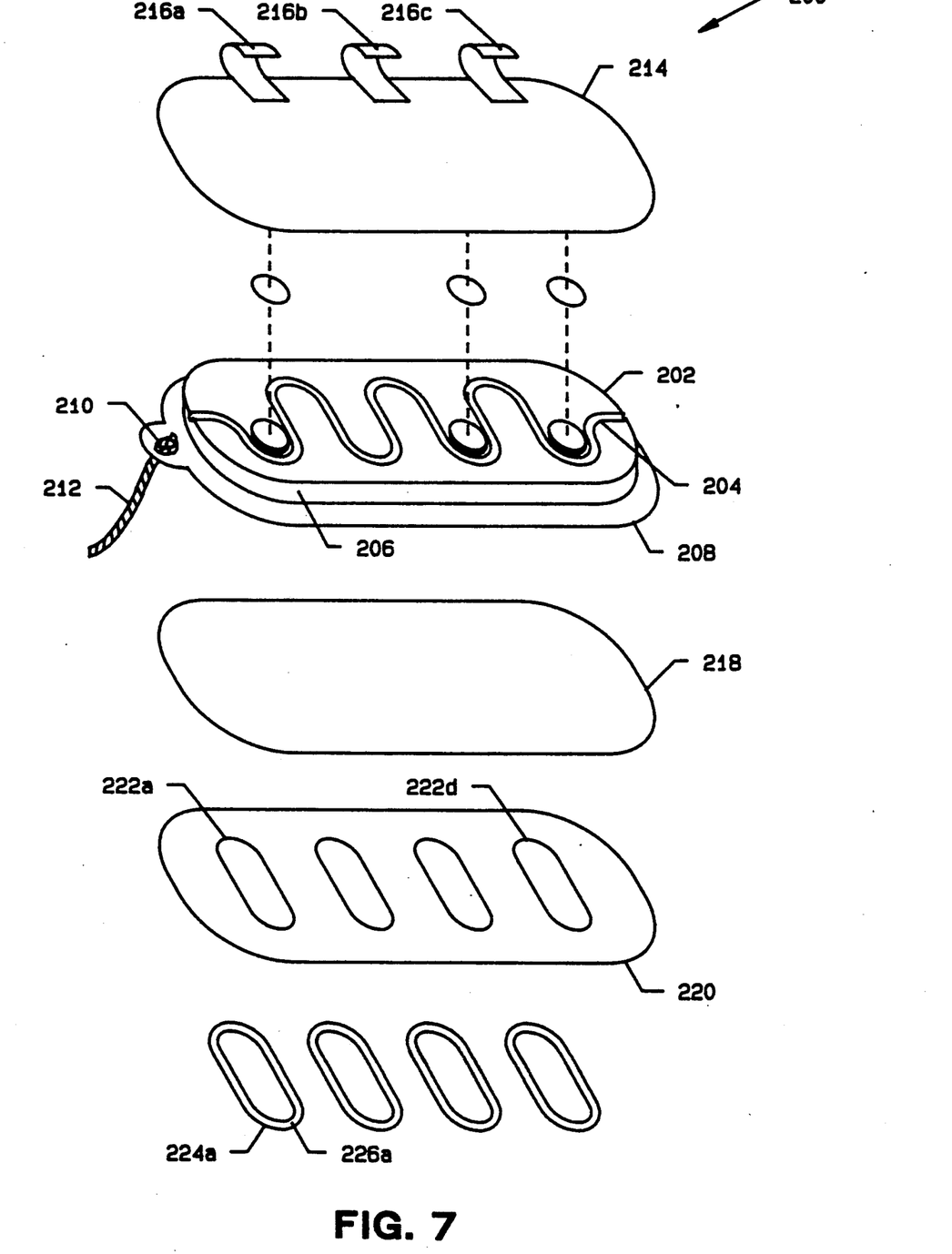

FIG. 7 illustrates an exploded view of a second alternative embodiment 200 including a blow molded, or other forming process such as vacuum forming, geometrically conforming container body 202 with a serpentine path 204, internal cavity volume 206, and an optional sealing edge 208. A hole 210 and hanging cord 212 are provided at one end. A cover 214 is hinged by tape tabs 216a–216c to the body 202. An air-permeable membrane 218 such as Tyvek secures, such as by adhesive, to the bottom of the container body 202. A non-permeable membrane 220 with a plurality of windows 222a–222d provides for passage of air to a chemical mix 223 in the container body 202. Any number of windows can be utilized. Pull tabs 224a–224d with securing adhesive 226a–226d secure over the windows 222a–222d, and pulls away in operation to expose the chemical mix to air to initiate a thermal reaction.

Various modifications can be made to the present invention without departing from the apparent scope hereof.

The present invention can also be utilized in industrial/commercial applications where the chemical container is shaped to engage around or about parts, such as fuel lines, flow control valves, pipes, etc., that need to be warmed or deiced. The shell can be designed in many configurations to provide a cavity to hold the chemicals, and an air-permeable membrane to allow diffusion of gases into the shell to cause heating reaction. The present invention can be utilized in industrial, military, commercial or consumer applications, as well as medical applications such as paramedics, first aid, etc.

We claim:

1. Fluid warmer comprising:
   a. flanged air cavity member with at least one hole;
   b. windowed membrane having a predetermined open cross section and the same dimensions as said air cavity member;
   c. air-permeable membrane having dimensions substantially the same as said air cavity member;
   d. flanged chemical cavity member and of the same dimensions as said air cavity member;
   e. a quantity chemically reactive mix in said chemical cavity chamber; and
   f. an inert atmosphere maintained in said air cavity member and said chemical cavity member by heat sealed flanges and sealing of said hole by said adhesive foil tape, and said adhesive foil tape means covering said hole.

2. Warmer of claim 1 wherein said chemical cavity member, said windowed membrane, and said air cavity member are of a heated chemically resistant polymer.

3. The fluid warmer of claim 1 wherein said chemically reactive mix comprises by weight:
   a. iron powder, 15%–40%;
   b. activated charcoal, 5%–30%;
   c. CaCl H O Calcium Chloride Dihydrate, 5%–20%;
   d. dried wood flour, 20%–40%; and,
   e. water, 10%–30%.

4. Fluid warmer for warming blood comprising:
   a. flanged air cavity member with at least one hole;
   b. windowed membrane having a predetermined open cross section and the same dimensions as said air cavity member;
   c. air-permeable membrane having dimensions substantially the same as said air cavity member;
   d. flanged chemical cavity member and of the same dimensions as said air cavity member;
   e. a quantity chemically reactive mix in said chemical cavity chamber; and,
   f. an inert atmosphere maintained in said air cavity member and said chemical cavity member by said heat sealed flanges and sealing of said hole by foil tape, and said securing foil tape means covering said hole.

5. Process of manufacturing a fluid warmer comprising the steps of:
   a. filling a chemical cavity member with dry chemically reactive powder mix;
   b. positioning said chemical cavity member, an air-permeable membrane, a windowed membrane, and an air cavity together in alignment about respective perimeters;
   c. heat sealing said perimeters, thereby forming a flange seal about the warmer;
   d. flooding said warmer with nitrogen in an inert atmosphere;
   e. adding water; and,
   f. taping and sealing holes in said air cavity.

6. Process of manufacturing a fluid warmer comprising the steps of:
   a. filling a cavity member with dry chemically reactive powder mix;
   b. positioning an air-permeable membrane, a windowed membrane in alignment about respective perimeters of said cavity member and securing same;
   c. containing said warmer in an air tight non-permeable pouch rather than sealing holes in said air cavity; and
   d. flooding said warmer with nitrogen in an inert atmosphere in a pouch.

7. A fluid warmer comprising:
   a. a bottle container to hold the chemical mixture with a cap;
   b. trough configuration molded into body surface of said bottle;
   c. chemically reactive mix inside said bottle;
   d. air-permeable membranes covering holes in said bottle for influx of air; and,
   e. non-permeable peel-off membrane to cover air-permeable membranes until ready to use.

* * * * *